United States Statutory Invention Registration [19]

[11] Reg. Number: H811

Nasu et al. [43] Published: Aug. 7, 1990

[54] BIOCIDAL COMPOSITION

[75] Inventors: Rikuo Nasu, Kyoto; Terumasa Komyoji, Shiga; Toshio Nakajima, Shiga; Kazumi Suzuki, Shiga; Keiichiro Ito, Shiga; Tekeshi Ohshima, Shiga; Hideshi Yoshimura, Osaka, all of Japan

[73] Assignee: Ishihara Sangyo Kaisha Ltd., Osaka, Japan

[21] Appl. No.: 322,460

[22] Filed: Mar. 13, 1989

[30] Foreign Application Priority Data

Mar. 11, 1988 [JP] Japan ..... 63-57920
Sep. 13, 1988 [JP] Japan ..... 63-229327

[51] Int. Cl.[5] ..... A01N 43/48; A01N 41/02; A01N 33/10

[52] U.S. Cl. ..... 514/92; 514/531; 514/476; 514/519; 514/493

[56] References Cited

FOREIGN PATENT DOCUMENTS 0298196 3/1988 European Pat. Off. .

*Primary Examiner*—John F. Terapane
*Assistant Examiner*—Joseph D. Anthony
*Attorney, Agent, or Firm*—Sughrue, Mion, Zinn, Macpeak & Seas

[57] ABSTRACT

A biocidal composition containing, as active ingredients, at least one imidazole compound represented by formula (I):

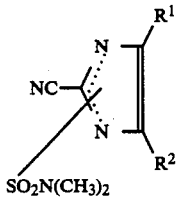

(I)

wherein $R^1$ represents a phenyl group, a halogen-substituted phenyl group, an alkyl group, or a halogen-substituted alkyl group; and $R^2$ represents a halogen atom, and at least one other specific compound. The combination of the compound represented by formula (I) and other specific compound can produce an unexpected effect in amount required and biocidal spectrum.

3 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

BIOCIDAL COMPOSITION

FIELD OF THE INVENTION

This invention relates to a biocidal composition containing as active ingredients at least one imidazole compound of formula (I) shown below and at least one other specific compound.

BACKGROUND OF THE INVENTION

The imidazole compounds of formula (I) shown below are useful as a biocide for controlling harmful organisms, which were found by the inventors of the present invention as described in European Patent 298,196A.

On the other hand, most of the compounds which are to be combined with the imidazole compounds of formula (I) have already been known to be effective as a fungicide, an insecticide, etc.

The imidazole compounds of formula (I) and many other biocides so far proposed each produces the respective characteristic biocidal effects on the respective objects. Some of them exert insufficient biocidal effects on specific harmful organisms, or some of them produce slightly inferior curative effects as compared with their preventive effects, or some of them are relatively short in their residual effect. Hence, the biocidal effects exhibited by these biocides on harmful organisms are sometimes unsatisfactory for practical utility depending on the occasion of application.

SUMMARY OF THE INVENTION

In the light of the above-described problem, the inventors of the present invention have conducted extensive investigations and, as a result, it has now been found that a combination of the imidazole compound represented by formula (I) shown below and other specific biocidal compound brings about unexpected results such as reduced amount of each compound to be used and enlarged biocidal spectrum of each compound as compared with the use of each compound alone.

The present invention relates to a biocidal composition for controlling harmful organisms containing, as active ingredients, at least one imidazole compound represented by formula (I):

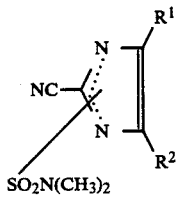

(I)

wherein $R^1$ represents a phenyl group, a halogen-substituted phenyl group, an alkyl group, or a halogen-substituted alkyl group; and Rz represents a halogen atom, and at least one compound selected from the group consisting of azole compounds, quinoxaline compounds, dithiocarbamate compounds, organic chlorine compounds, benzimidazole compounds, pyridinamine compounds, cyanoacetamide compounds, phenylamide compounds, sulfenic acid compounds, copper compounds, isoxazole compounds, organophosphorus compounds, N-halogenothioalkyl compounds, dicarboximide compounds, benzanilide compounds, benzamide compounds, piperazine compounds, pyridine compounds, pyrimidine compounds, piperidine compounds, morpholine compounds, organotin compounds, urea compounds, cinnamic acid compounds, carbamate compounds, pyrethroid compounds, benzoylurea compounds, thiazolidine compounds, thiadiazine compounds, nereistoxin derivatives, pyridazinone compounds, and spores of *Bacillus thurinqiensis* and crystalline toxin produced thereby.

DETAILED DESCRIPTION OF THE INVENTION

In formula (I), the halogen atom includes fluorine, chlorine, bromine, and iodine atoms.

Further, in formula (I), the alkyl group contains from 1 to 4 carbon atoms and mention may be made of, for example, methyl group, ethyl group, n-propyl group, isopropyl group, n-butyl group, sec-butyl group, isobutyl group, tert-butyl group, etc.

As to the present invention, preferred embodiments are illustrated below.

(1) A biocidal composition wherein the compound which is used in admixture with the imidazole compounds represented by formula (I) is at least one compound selected from the group consisting of azole compounds, quinoxaline compounds, dithiocarbamate compounds, organic chlorine compounds, benzimidazole compounds, pyridinamine compounds, cyanoacetamide compounds, phenylamide compounds, sulfenic acid compounds, copper compounds, isoxazole compounds, organophosphorus compounds, dicarboximide compounds, benzanilide compounds, and benzamide compounds.

(2) A biocidal composition wherein the compound which is used in admixture with the imidazole compounds represented by formula (I) is at least one compound selected from the group consisting of 1-[N-(4-chloro-2-trifluoromethylphenyl)-2-propoxyacetimidoyl]imidazale [triflumizole], 6-methyl-1,3-dithiolo[4,5-b]quinoxalin-2-one [chinomethionate], a complex of zinc and manganese ethylenebis(dithiocarbamate) [mancozeb], tetrachloroisophthalonitrile [chlorothalonil], methyl 1-(butyl-carbamoyl)benzimidazol-2-yl carbamate [benomyl], 3-chloro-N-(3-chloro-2,6-dinitro-4-α,α,α-trifluorotolyl)-5-trifluoromethyl-2-pyridinamine [fluazinam], 1-(2- cyano-2-methoxyiminoacetyl)-3-ethylurea [cymoxanil], methyl N-(2-methoxyacetyl)-N-(2,6-xylyl)-DL-alaninate [metalaxyl], 2-methoxy-N-(2-oxo-1,3-oxazolidin-3-yl)- acet-2′,6′-xylidide [oxadixyl], N-dichlorofluoro- methylthio-N′,N′-dimethyl-N-phenylsulphamide [dichlofluanid], copper hydroxide [copper hydroxide], 5-methyl- isoxazol-3-ol [hydroxyisoxazole], aluminum tris(ethyl phosphonate) [fosetyl-Al], N-(3,5-dichlorophenyl)-1,2-dimethylcyclopropane-1,2-dicarboximide [procymidone], α,α,α-trifluoro-3′-isopropoxy-o-toluanilide [flutolanil], and (RS)-4-chloro-N-[cyano(ethoxy)methyl]benzamide.

(3) A biocidal composition wherein the imidazole compound is represented by formula (I′):

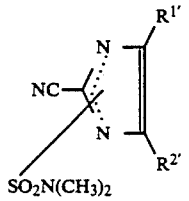

(I')

wherein $R^{1'}$ represents a phenyl group or a halogen-substituted alkyl group; and $R^{2'}$ represents a chlorine atom.

(4) A biocidal composition whose main use is for a fungicide.

The imidazole compounds represented by formula (I) include compounds represented by formula (I-a) and/or compounds represented by formula (I-b):

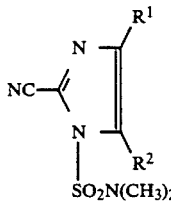

(I-a)

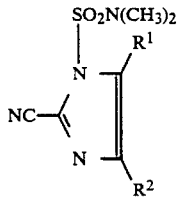

(I-b)

Typical examples of the imidazole compounds of formula (I) are shown in Table 1 below.

TABLE 1

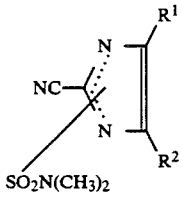

(I)

| Compound No.* | $R^1$ | $R^2$ | Physical Property |
|---|---|---|---|
| A-lb | phenyl | Cl | m.p. 109–112° C. |
| A-2b | 2-chlorophenyl | Cl | m.p. 113–117° C. |
| A-3 | 2-fluorophenyl | Cl | m.p. 96–101° C. |
| A-4 | 4-chlorophenyl | Cl | m.p. 108° C. |
| A-5b | ethyl | Cl | m.p. 95–97° C. |
| A-6b | n-propyl | Cl | m.p. 64–66° C. |
| A-7b | n-butyl | Cl | m.p. 48–49° C. |
| A-8b | n-propyl | Br | m.p. 93–94° C. |
| A-9b | 3-fluroropropyl | Cl | m.p. 75–79° C. |
| A-10b | 3-brompropyl | Cl | m.p. 79–84° C. |
| A-11b | 4-chlorobutyl | Cl | $n_D^{22.1}$1.5382 |
| A-12b | 3-chloropropyl | Cl | m.p. 102–105° C. |
| A-13b | 2-chloroethyl | Cl | m.p. 92–94° C. |

Note:

*The compounds having compound numbers with a mark "b" are included under the formula (I-b) and those with no mark are mixtures of compounds under the formulae (I-a) and (I-b).

Examples of the compounds which can be used in combination with the imidazole compounds of formula (I) are tabulated below.

| Compound No. | Compound Name | Common Name |
|---|---|---|
| Azole Compounds: | | |
| B-1 | 1-(4-Chlorophenoxy)-3,3-dimethyl-1-(1H-1,2,4-triazol-1-yl)butanone | Triadimefon |
| B-2 | 1-(Biphenyl-4-yloxy)-3,3-dimethyl-1-(1H-1,2,4-triazol-1-yl)-butan-2-ol | Bitertanol |
| B-3 | 1-[N-(4-Chloro-2-trifluoromethylphenyl)-2-propoxyacetimidoyl]-imidazole | Triflumizole |
| B-4 | 1-[2-(2,4-Dichlorophenyl)-4-ethyl-1,3-dioxolan-2-ylmethyl]-1H-1,2,4-triazole | Etaconazole |
| B-5 | 1-[2-(2,4-Dichlorophenyl)-4-propyl-1,3-dioxolan-2-ylmethyl]-1H-1,2,4-triazole | Propiconazole |
| B-6 | 1-[2-(2,4-Dichlorophenyl)pentyl]-1H-1,2,4-triazole | Penconazole |
| B-7 | Bis(4-fluorophenyl)(methyl)(1H-1,2,4-triazol-1-ylmethyl)silane | Flusilazole |
| B-8 | 2-(4-Chlorophenyl)-2-(1H-1,2,4-triazol-1-ylmethyl)hexanenitrile | Myclobutanil |
| B-9 | (2RS, 3RS)-2-(4-Chlorophenyl)-3-cyclopropyl-1-(1H-1,2,4-triazol-1-yl)butan-2-ol | Cyproconazole |
| B-10 | (RS)-1-(4-Chlorophenyl)-4,4-dimethyl-3-(1H-1,2,4-triazol-1-ylmethyl)pentan-3-ol | Terbuconazole |
| B-11 | (RS)-2-(2,4-Dichlorophenyl)-1-(1H-1,2,4-triazol-1-yl)hexan-2-ol | Hexaconazole |
| B-12 | (2RS, 5RS)-5-(2,4-Dichlorophenyl)tetrahydro-5-(1H-1,2,4-triazol-1-ylmethyl)-2-furyl 2,2,2-trifluoroethyl ether | Furconazole-cis |
| B-13 | N-Propyl-N-[2-(2,4,6-trichlorophenoxy)ethyl]imidazole-1-carboxamide | Prochloraz |
| Quinoxaline Compounds: | | |
| C-1 | 6-Methyl-1,3-dithiolo[4,5-b]-quinoxalin-2-one | Chinomethionate |
| Dithiocarbamate Compounds: | | |
| D-1 | Manganese ethylenebis(dithiocarbamate) polymer | Maneb |
| D-2 | Zinc ethylenebis(dithiocarbamate) polymer | Zineb |
| D-3 | Complex of zinc and manganese ethylenebis(dithiocarbamate) (Maneb) | Mancozeb |
| D-4 | Dizinc bis(dimethyldithio)-carbamate) ethylenebis-(dithiocarbamate) | Polycarbamate |
| D-5 | Zinc propylenebis(dithiocarbamate) polymer | Propineb |
| Organic Chlorine Compounds: | | |
| E-1 | 4,5,6,7-Tetrachlorophthalide | Fthalide |
| E-2 | Tetrachloroisophthalonitrile | Chlorothalonil |
| E-3 | Pentachloronitrobenzene | Quintozene |
| E-4 | 2,2,2-Trichloro-1,1-bis(4-chlorophenyl)ethanol | Dicofol |
| Benzimidazole Compounds: | | |
| F-1 | Methyl 1-(butylcarbamoyl)benzimidazol-2-yl carbamate | Benomyl |
| F-2 | Dimethyl 4,4'-(o-phenylene)-bis-(3-thioallophanate) | Thiophanate-methyl |
| F-3 | Methyl benzimidazol-2-ylcarbamate | Carbendazim |
| Pyridinamine Compounds: | | |
| G-1 | 3-Chloro-N-(3-chloro-2,6-dinitro-4-α,α,α-trifluorotolyl)-5-trifluoromethyl-2-pyridinamine | Fluazinam |
| Cyanoacetamide Compounds: | | |
| H-1 | 1-(2-Cyano-2-methoxyiminoacetyl)- | Cymoxanil |

-continued

| Compound No. | Compound Name | Common Name |
|---|---|---|
| | 3-ethylurea | |
| Phenylamide Compounds: | | |
| I-1 | Methyl N-(2-methoxyacetyl)-N-(2,6-xylyl)-DL-alaninate | Metalaxyl |
| I-2 | 2-Methoxy-N-(2-oxo-1,3-oxazolidin-3-yl)acet-2',6'-xylidide | Oxadixyl |
| I-3 | (±)-α-2-Chloro-N-(2,6-xylylacetamide)-γ-butyrolactone | Ofurace |
| I-4 | Methyl N-phenylacetyl-N-(2,6-xylyl)-DL-alaninate | Benalaxyl |
| I-5 | Methyl N-(2-furoyl)-N-(2,6-xylyl)-DL-alaninate | Furalaxyl |
| I-6 | (±)-α-[N-(3-Chlorophenyl)cyclopropane-carboxamide]-γ-butyrolactone | Cyprofuram |
| Sulfenic Acid Compounds: | | |
| J-1 | N-Dichlorofluoromethylthio-N',N'-dimethyl-N-phenylsulphamide | Dichlofluanid |
| Copper Compounds: | | |
| K-1 | Copper hydroxide | Copper Hydroxide |
| K-2 | Copper-8-quinolinolate | Oxine-copper |
| Isoxazole Compounds: | | |
| L-1 | 5-Methylisoxazol-3-ol | Hydroxyisoxazole |
| Organophosphorus Compounds: | | |
| M-1 | Aluminum tris(ethyl phosphonate) | Fosetyl-Al |
| M-2 | O-2,6-Dichloro-p-tolyl-O,O-dimethyl phosphorothioate | Tolclofos-methyl |
| M-3 | (RS)-S-(RS)-Sec-butyl-O-ethyl-2-oxo-2-thiazolidinyl-phosphonothioate | disclosed in U.S. Pat. No. 4,590,182 |
| M-4 | O,S-Dimethyl acetylphosphoramidothioate | Acephate |
| M-5 | 2,2-Dichlorovinyl dimethyl phosphate | Dichlorvos |
| M-6 | O-2,4-Dichlorophenyl O-ethyl S-propyl phosphorodithioate | Prothiofos |
| N-Halogenothioalkyl Compounds: | | |
| N-1 | N-(Trichloromethylthio)cyclohex-4-ene-1,2-dicarboximide | Captan |
| N-2 | N-(1,1,2,2-Tetrachloroethylthio)cyclohex-4-ene-1,2-dicarboximide | Captafol |
| N-3 | N-(Trichloromethylthio)phthalimide | Folpet |
| Dicarboximide Compounds: | | |
| O-1 | N-(3,5-Dichlorophenyl)-1,2-dimethylcyclopropane-1,2-dicarboximide | Procymidone |
| O-2 | 3-(3,5-Dichlorophenyl)-N-isopropyl-2,4-dioxoimidazolidine-1-carboxamide | Iprodione |
| O-3 | (RS)-3-(3,5-Dichlorophenyl)-5-methyl-5-vinyl-1,3-oxazolidine-2,4-dione | Vinclozolin |
| Benzanilide Compounds: | | |
| P-1 | α,α,α-Trifluoro-3'-isopropoxy-o-toluanilide | Flutolanil |
| P-2 | 3'-Isopropoxy-o-toluanilide | Mepronil |
| Benzamide Compounds: | | |
| Q-1 | (RS)-4-Chloro-N-[cyano(ethoxy)-methyl]benzamide | disclosed in U.S. Pat. No. 4,447,446 |
| Q-2 | 2-(1,3-Dimethylpyrazol-4-yl-carbonylamino)-4-methyl-3-pentenenitrile | disclosed in British Patent 2,190,375 |
| Q-3 | α-(Nicotinylamino)-(3-fluorophenyl)acetonitrile | disclosed in JP-A-63-135364 |

(The term "JP-A" as used herein means a "published unexamined patent application".)

| Compound No. | Compound Name | Common Name |
|---|---|---|
| Piperazine Compounds: | | |
| R-1 | N,N'-[Piperazine-1,4-diylbis-[(trichloromethyl)methylene]]-diformamide | Triforine |
| Pyridine Compounds: | | |
| S-1 | 2',4'-Dichloro-2-(3-pyridyl)-acetophenone O-methyloxime | Pyrifenox |
| Pyrimidine Compounds: | | |
| T-1 | (±)-2,4'-Dichloro-α-(pyrimidin-5-yl)benzhydryl alcohol | Fenarimol |
| Piperidine Compounds: | | |
| U-1 | (RS)-1-[3-(4-Tert-butylphenyl)-2-methylpropyl]piperidine | Fenpropidin |
| Morpholine Compounds: | | |
| V-1 | (±)-Cis-4-[3-(4-tert-butylphenyl)-2-methylpropyl]-2,6-dimethylmorpholine | Fenpropimorph |
| Organotin Compounds: | | |
| W-1 | Triphenyltin hydroxide | Fentin hydroxide |
| W-2 | Triphenyltin acetate | Fentin acetate |
| Urea Compounds: | | |
| X-1 | 1-(4-Chlorobenzyl)-1-cyclopentyl-3-phenylure | Pencycuron |
| Cinnamic Acid Compounds: | | |
| Y-1 | (E,Z)4-[3-(4-Chlorophenyl)-3-(3,4-dimethoxyphenyl)acryloyl] morpholine | Dimethomorph |
| Carbamate Compounds: | | |
| Za-1 | 1-Naphthyl methylcarbamate | Carbaryl |
| Za-2 | S-Methyl N-(methylcarbamoyloxy)-thioacetimidate | Methomyl |
| Za-3 | 2-Ethylthiomethylphenyl methylcarbamate | Ethiofencarb |
| Za-4 | Ethyl N-benzyl-N-[[methyl-[[(Z)-1-methylthioethylidene]-aminooxycarbonyl]amino]thio]-β-alaninate | ORION ® (trade name) |
| Pyrethroid Compounds: | | |
| Zb-1 | (RS)-α-Cyano-3-phenoxybenzyl (Z)-(1RS, 3RS)-(2-chloro-3,3,3-trifluoropropenyl)-2,2-dimethylcyclopropanecarboxylate | Cyhalothrin |
| Zb-2 | 2,3,5,6-Tetrafluoro-4-methylbenzyl (Z)-(1RS, 3RS)-3-(2-chloro-3,3,3-trifluoroprop-1-enyl)-2,2-dimethylcyclopropanecarboxylate | Tefluthrin |
| Zb-3 | 2-(4-Ethoxyphenyl)-2-methylpropyl-3-phenoxybenzyl ether | Ethofenprox |
| Zb-4 | (RS)-α-Cyano-3-phenoxybenzyl (1RS, 3RS; 1RS, 3SR)-3-(2,2-dichlorovinyl)-2,2-dimethylcyclopropanecarboxylate | Cypermethrin |
| Benzoylurea Compounds: | | |
| Zc-1 | 1-(4-Chlorophenyl)-3-(2,6-difluorobenzoyl)urea | Diflubenzuron |
| Zc-2 | 1-(3,5-Dichloro-2,4-difluorophenyl)-3-(2,6-difluorobenzoyl)-urea | Teflubenzuron |
| Zc-3 | 1-[3,5-Dichloro-4-(3-chloro-5-trifluoromethyl-2-pyridyloxy)-phenyl]-3-(2,6-difluorobenzoyl)-urea | Chlorfluazuron |
| Thiazolidine Compounds: | | |
| Zd-1 | (4RS, 5RS)-5-(4-Chlorophenyl)-N-cyclohexyl-4-methyl-2-oxo-1,3-thiazolidine-3 carboxamide | Hexythiazox |
| Thiadiazine Compounds: | | |
| Ze-1 | 2-Tert-butylimino-3-isopropyl-5-phenyl-1,3,5-thiadiazinan-4-one | Buprofezin |
| Nereistoxin Derivatives | | |
| Zf-1 | N,N-Dimethyl-1,2,3-trithian-5-ylamine | Thiocyclam |
| Zf-2 | S,S'-2-Dimethylaminotri- | Cartap |

-continued

| Compound No. | Compound Name | Common Name |
|---|---|---|
| | methylene bis(thiocarbamate) | |
| Pyridazinone Compounds: | | |
| Zg-1 | 2-Tert-butyl-5-(4-tert-butylbenzylthio)-4-chloropyridazin-3(2H)-one | disclosed in European Patent 134,439 |
| Spores of *Bacillus thuringiensis* and crystalline toxin produced thereby: | | |
| | Name of Pathogen | |
| Zh-1 | *Bacillus thuringiensis* subsp, Kurstaki, HD-1 | THURICIDE ® (trade name) |

The imidazole compounds represented by formula (I) can be prepared, for example, by the following reaction schemes.

Process A

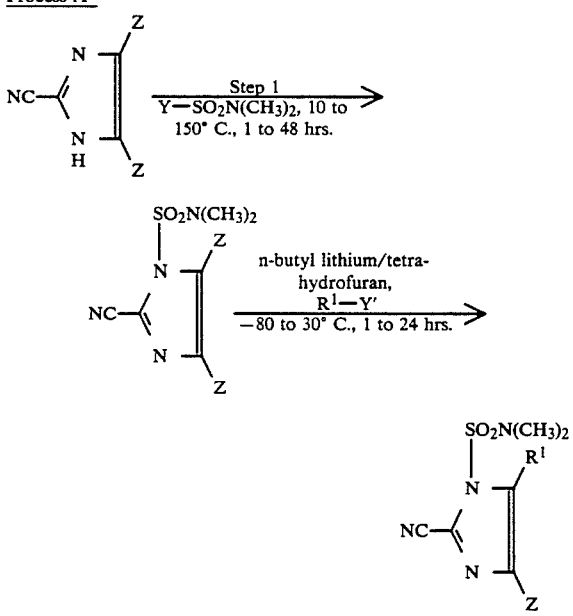

wherein Z represents a hydrogen atom, a chlorine atom, or a bromine atom; Y represents a chlorine atom, a fluorine atom, a bromine atom, or an iodine atom; Y' represents a chlorine atom, a bromine atom, or an iodine atom; and $R^1$ is as defined above.

Process B

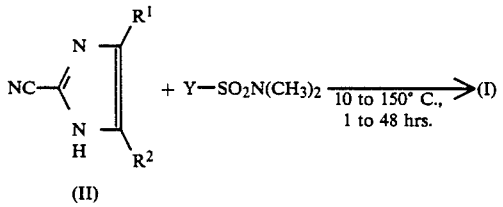

wherein Y, $R^1$, and $R^2$ are as defined above.

Step 1 of process A and Process B are carried out, if desired, in the presence of a solvent and an acid acceptor.

The solvent which can be used includes aromatic hydrocarbons, e.g., benzene, toluene, xylene, chlorobenzene, etc.; cyclic or acyclic aliphatic hydrocarbons, e.g., chloroform, carbon tetrachloride, methylene chloride, dichloroethane, trichloroethane, n-hexane, cyclohexane, etc.; ethers, e.g., diethyl ether, dioxane, tetrahydrofuran, etc.; ketones, e.g., acetone, methyl ethyl ketone, methyl isobutyl ketone, etc.; nitriles, e.g., acetonitrile, propionitrile, etc.; and aprotic polar solvents, e.g., dimethylformamide, N-methylpyrrolidone, dimethyl sulfoxide, sulfolane, etc.

The acid acceptor which can be used includes inorganic bases such as alkali metal hydroxides, e.g., sodium hydroxide and potassium hydroxide, alkali metal or alkaline earth metal carbonates, e.g., anhydrous potassium carbonate and anhydrous calcium carbonate, alkali metal hydrides, e.g., sodium hydride, and alkali metals, e.g., metallic sodium; and organic basis, e.g., triethylamine.

The reactions of Step 1 of Process A and Process B can be effected in the presence of an appropriate catalyst, such as a phase transfer catalyst (e.g., quaternary ammonium salt derivatives).

The compound represented by formula (II), the starting compounds of Process B, can be prepared according to the following process or processes similar thereto.

Process C

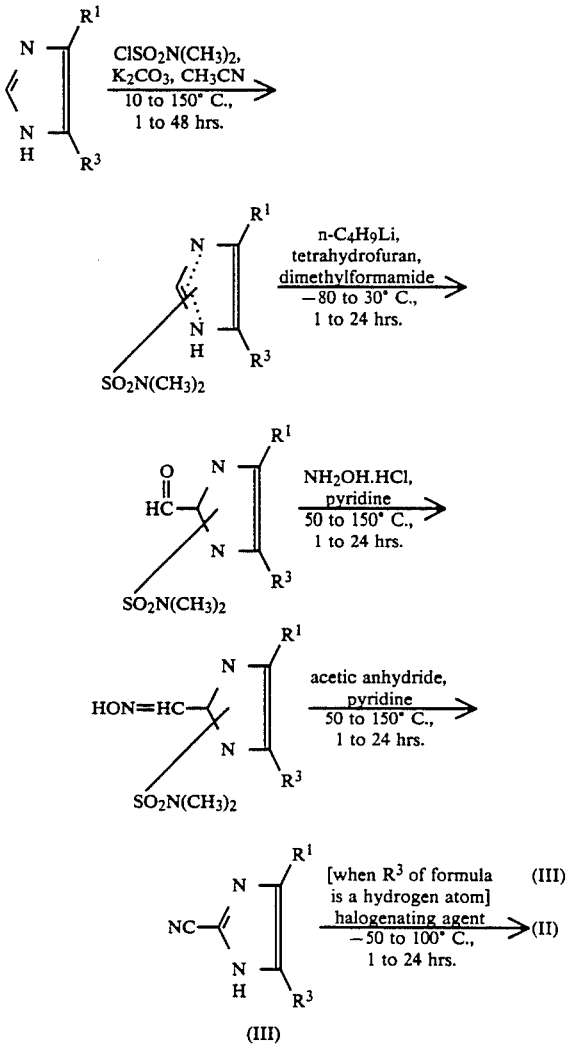

wherein $R^3$ represents a hydrogen atom or a halogen atom; and $R^1$ is as defined above.

The compound of formula (II) includes tautomers represented by the following formulae:

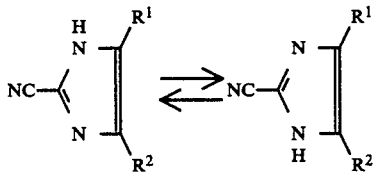

wherein $R^1$ and $R^2$ are as defined above.

Accordingly, in cases where the compound of formula (I) is prepared by starting with the compound of formula (II), the compounds having formulae (I-a) and/or (I-b) can be obtained.

Thus, the reaction of introducing $-SO_2N(CH_3)_2$ group to the starting compound including tautomers yields either one of the two isomers or a mixture thereof. Whether a mixture of tautomers or either one of the tautomers is obtained depends on the starting compound, the reaction process of from the starting compound through the product, the reaction conditions, and the like. In the case where a mixture is obtained, the mixing ratio is also determined by these factors.

Synthesis Examples of the imidazole compounds of formula (I) are exemplified below.

SYNTHESIS EXAMPLE 1

Synthesis of 4-chloro-2-cyano-1-dimethyl-sulfamoyl-5-n-propylimidazole (Compound No. A-6b)

(1) 2-Formyl-1-diethoxymethylimidazole was obtained as an oily substance from 1-diethoxymethylimidazole in accordance with the method described in *J. Org. Chem.*, Vol. 45, 4038-4040 (1980). The resulting compound was reacted with hydroxylamine hydrochloride-sodium acetate in water to obtain imidazole-2-aldoxime, which was then dehydrated with acetic anhydride to obtain 2-cyanoimidazole having a melting point of 176° C.

(2) Thirty grams of 2-cyanoimidazole as obtained in (1) above, 53.4 g of anhydrous potassium carbonate, and 600 ml of acetonitrile were mixed at room temperature, and the mixture was allowed to react at reflux for 2 hours. After cooling, 55.6 g of dimethylsulfamoyl chloride was added thereto, and the reaction at reflux was continued for an additional period of 2 hours.

After completion of the reaction, the reaction mixture was poured into water and extracted with methylene chloride. The extract was washed with water and dried over anhydrous sodium sulfate. The solvent was removed by distillation, and the residue was purified by silica gel column chromatography using methylene chloride as a developing solvent to obtain 28.0 g of 2-cyano-1-dimethylsulfamoylimidazole having a melting point of from 74 to 76° C.

(3) In a four-necked flask were charged in a nitrogen atmosphere 12.0 g of 2-cyano-1-dimethylsulfamoylimidazole as obtained in (2) above and 240 ml of anhydrous tetrahydrofuran, and 41.3 ml of a 1.6M n-butyl lithium-hexane solution (produced by Aldrich) was gradually added dropwise to the mixture while maintaining at a temperature of −75° C. or lower with dry ice-acetone. After the dropwise addition, the mixture was kept at that temperature for 15 minutes, and 30 ml of a tetrahydrofuran solution of 15.3 g of n-propyl iodide was added dropwise thereto at −70° C. or lower. After the dropwise addition, the reaction mixture was stirred overnight to gradually elevate the temperature to room temperature.

After completion of the reaction, the reaction mixture was poured into water and extracted with 500 ml of ethyl acetate. The ethyl acetate layer was washed with water and dried over anhydrous sodium sulfate. The ethyl acetate was removed by distillation, and the residue was purified by silica gel column chromatography using methylene chloride as a developing solvent and separated to give 4.8 g of 2-cyano-1-dimethylsulfamoyl-5-n-propylimidazole having a melting point of from 51 to 52° C.

(4) 4.8 g of 2-cyano-1-dimethylsulfamoyl-5-n-propylimidazole as obtained in (3) above, 40 ml of pyridine, and 11.4 g of pyridinium chloride were mixed, and the mixture was stirred at 90° C. for 4 hours.

After completion of the reaction, the pyridine was removed by distillation from the reaction mixture, and the residue was extracted with ethyl acetate. The extract was washed with water and then dried over anhydrous sodium sulfate. Thereafter, the ethyl acetate was removed by distillation, and the residue was purified by silica gel column chromatography (developing solvent: a mixture of ethyl acetate and n-hexane) and separated to give 2.46 g of 2-cyano-4(5)-n-propylimidazole having a melting point of from 52 to 54° C.

(5) 2.35 g of 2-cyano-4(5)-n-propylimidazole as obtained in (4) above, 80 ml of chloroform, and 2.6 g of N-chlorosuccinimide were mixed, and the mixture was reacted at the reflux temperature for 4 hours.

After completion of the reaction, 200 ml of water was added to the reaction mixture. The resulting organic layer was washed with water and then dried over anhydrous sodium sulfate. The chloroform was removed by distillation, and the residue was purified by silica gel column chromatography (developing solvent: a 1:1 mixture of ethyl acetate and n-hexane) and separated to give 2.2 g of 4(5)-chloro-2-cyano-5(4) n-propylimidazole having a melting point of from 107 to 109° C.

(6) 2.0 g of 4(5)-chloro-2-cyano-5(4)-n-propylimidazole as obtained in (5) above, 30 ml of acetonitrile, 1.95 g of anhydrous potassium carbonate, and 1.86 g of dimethylsulfamoyl chloride were mixed, and after gradually elevating the temperature, the mixture was reacted at the reflux temperature for 1 hour.

After completion of the reaction, the acetonitrile was removed by distillation from the reaction mixture. After pouring 100 ml of water into the residue, the resulting mixture was extracted with 50 ml of methylene chloride. The extract was washed with water and dried over anhydrous sodium sulfate. The methylene chloride was removed by distillation, and the residue was allowed to stand overnight at room temperature. The analysis of the residue revealed that one of the two isomers in the mixture decomposed and returned to the starting 4(5)-chloro-2-cyano-5(4)-n-propylimidazole. The residue containing the other isomer was purified by silica gel column chromatography (developing solvent: methylene chloride) and separated to give 1.1 g of 4-chloro-2-cyano-1-dimethylsulfamoyl-5-n-propylimidazole (Compound No. A-6b) having a melting point of from 64° to 66° C.

SYNTHESIS EXAMPLE 2

Synthesis of 4-chloro-2-cyano-1-dimethylsulfamoyl-5-phenylimidazole (Compound No. A-1b)

(1) In 100 ml of chloroform was dissolved 1.352 g of 2-cyano-4(5)-phenylimidazole, and 1.175 g of N-chlorosuccinimide was added to the solution. The mixture was reacted upon heating at the reflux temperature for 4 hours.

After completion of the reaction, the reaction mixture was poured into water and extracted with chloroform. After washing with water, the extracted layer was dried over anhydrous sodium sulfate. The solvent was distilled off under reduced pressure, and the residue was purified by silica gel column chromatography (developing solvent: methylene chloride) to give 1.28 g of 4(5)-chloro-2-cyano-5(4)-phenylimidazole having a melting point of from 149° to 151° C.

(2) In 6 ml of acetone was dissolved 0.43 g of 4(5)-chloro-2-cyano-5(4)-phenylimidazole as obtained in (1) above, and 0.29 g of anhydrous potassium carbonate and 0.36 g of dimethylsulfamoyl chloride were added to the solution. The mixture was reacted upon heating at the reflux temperature for 30 minutes.

After completion of the reaction, the reaction mixture was poured into water and extracted with ethyl acetate. After washing with water, the extracted layer was dried over anhydrous sodium sulfate. The solvent was distilled off under reduced pressure, and the residue was then purified by silica gel column chromatography (developing solvent: methylene chloride) to give 0.5 g of 4(5)-chloro-2-cyano-1-dimethylsulfamoyl-5(4)phenylimidazole having a melting point of from 106° to 109° C.

As a result of analysis by means of NMR spectra, the compound described above was found to be an isomeric mixture of 4-chloro-2-cyano-1-dimethylsulfamoyl-5-phenylimidazole and 5-chloro-2-cyano-1-dimethylsulfamoyl-4-phenylimidazole in almost equal ratios.

(3) After allowing to stand for 24 hours at room temperature, 2.9 g of the mixture of these isomers as obtained in a manner similar to (2) above was purified by silica gel column chromatography (developing solvent: methylene chloride) to give 1.15 g of 4-chloro-2-cyano-1-dimethylsulfamoyl-5-phenylimidazole (Compound No. A-1b) having a melting point of from 109° to 112° C. Further, by purification of and isolation from this compound, 0.7 g of 4(5)-chloro-2-cyano-5(4)-phenylimidazole was also obtained.

SYNTHESIS EXAMPLE 3

Synthesis of 4-chloro-5-(3-chloropropyl)-2-cyano-1-dimethylsulfamoylimidazole (Compound No. A-12b)

(1) In a four-necked flask were charged in a nitrogen atmosphere 9.4 g of 2-cyano-4,5-dichloro-1-dimethylsulfamoylimidazole and 152 ml of anhydrous tetrahydrofuran, and 28.6 ml of a 1.6 M n-butyl lithiumhexane solution was slowly added thereto while maintaining at a temperature of −75° C. or lower by cooling with dry ice-acetone. After the dropwise addition, the mixture was kept at that temperature for 15 minutes. Then, 31 ml of a tetrahydrofuran solution of 14.3 g of 1-chloro-3-iodopropane was added dropwise to the mixture at −70° C. or lower, followed by stirring at room temperature overnight to gradually elevate the temperature to room temperature.

After completion of the reaction, the reaction mixture was poured into water and extracted with methylene chloride. The extract was washed with water and dried over anhydrous sodium sulfate. The methylene chloride was removed by distillation, and the residue was purified by silica gel column chromatography once using methylene chloride and then using a mixture of n-hexane and ethyl acetate as developing solvents to obtain 4.1 g of 4-chloro-5-(3-chloropropyl)-2-cyano-1-dimethylsulfamoylimidazole (Compound No. A-12b) having a melting point of from 102° to 105° C.

The biocidal compositions according to the present invention, comprising the imidazole compound of formula (I) in combination with other specific compound, are particularly useful as agricultural fungicides. Specifically, they exhibit excellent effects of controlling diseases of crop plants such as rice blast caused by *Pyricularia oryzae*, rice sheath blight caused by *Rhizoctonia solani*, cucumber anthracnose caused by *Colletotrichum lagenarium*, cucumber powdery mildew caused by *Sphaerotheca fuliginea*, cucumber downy mildew caused by *Pseudoperonospora cubensis*, tomato late blight caused by *Phytophthora infestans*, tomato early blight caused by *Alternaria solani*, citrus melanose caused by *Diaporthe citri*, citrus common green mold caused by *Penicillium digitatum*, pear scab caused by *Venturia nashicola*, apple alternaria blotch caused by *Alternaria mali*, grape downy mildew caused by *Plasmopara viticola*, gray mold caused by *Botrytis cinerea*, sclerotinia rot caused by *Sclerotinia sclerotiorum*, rust, etc.; and soil diseases caused by phytopathogenic fungi such as Fusarium, Pythium, Rhizoctonia, Verticillium, Plasmodiophora, etc. In particular, the biocidal compositions of the present invention exhibit excellent effects of controlling diseases such as potato or tomato late blight caused by *Phytophthora infestans*, cucumber downy mildew caused by *Pseudoperonospora cubensis*, grape downy mildew caused by *Plasmopara viticola*, tobacco blue mold caused by *Peronospora tabacina;* and various soil diseases caused by phycomycetes such as Plasmodiophora, Aphanomyces, Pythium, etc.

The biocidal compositions of the present invention have a prolonged residual effect so that they exhibit an excellent preventive effect, and also exhibit an excellent curative effect as well. It is therefore possible to control diseases by treatment after infection. In addition, since they possess a systemic activity, it is also possible to control diseases of the stem and leaf by soil treatment.

Further, the biocidal compositions of the present invention show an excellent controlling effect against agriculturally and horticulturally harmful insects such as planthoppers, diamondback moth (*Plutella xylostella*), green rice leafhopper (*Nephotettix cincticeps*), adzuki bean weevil (*Callosobruchus chinensis*), common cutworm (*Spodoptera litura*), green peach aphid (*Myzus persicae*), etc.; mites such as twospotted spider mite (*Tetranychus urticae*), carmine spider mite (*Tetranychus cinnabarinus*), citrus red mite (*Panonychus citri*), etc.; and nematodes such as southern root-knot nematode (*Meloidogyne incognita*), *etc.*

The compounds constituting the biocidal composition of the present invention can be formulated into a variety of forms, such as emulsifiable concentrates, dusts, wettable powders, aqueous solutions, granules, suspension concentrates, etc., together with various adjuvants, as in conventional agricultural preparations.

The imidazole compound of formula (I) and the other specific compound may be mixed and formulated, or each of the compounds may be separately formulated and then mixed together. Upon use, the preparation may be used as such or as diluted with an appropriate diluent, e.g., water, to a predetermined concentration.

Examples of the adjuvants which can be used include carriers, emulsifying agents, suspending agents, dispersing agents, spreaders, penetrating agents, wetting agents, thickeners, stabilizers, etc. These adjuvants can be added appropriately according to necessity.

The carriers are classified into solid carriers and liquid carriers. The solid carriers include animal and vegetable powders, e.g., starch, sugar, cellulose powders, cyclodextrin, activated charcoal, soybean powders, wheat powders, chaff powders, wood powders, fish powders, powdery milk, etc., and mineral powders, e.g., talc, kaolin, bentonite, bentonite-alkylamine complexes, calcium carbonate, calcium sulfate, sodium bicarbonate, zeolite, diatomaceous earth, white carbon, clay, alumina, silica, sulfur powders, etc. The liquid carriers include water, animal and vegetable oils, e.g., soybean oil, cotton seed oil, etc., alcohols, e.g., ethyl alcohol, ethylene glycol, etc., ketones, e.g., acetone, methyl ethyl ketone, etc., ethers, e.g., dioxane, tetrahydrofuran, etc., aliphatic hydrocarbons, e.g., kerosene, lamp oil, liquid paraffin, etc., aromatic hydrocarbons, e.g., xylene, trimethylbenzene, tetramethylbenzene, cyclohexane, solvent naphtha, etc., halogenated hydrocarbons, e.g., chloroform, chlorobenzene, etc., acid amides, e.g., dimethylformamide, etc., esters, e.g., ethyl acetate, fatty acid glycerine esters, etc., nitriles,, e.g., acetonitrile, etc., sulfur-containing compounds, e.g., dimethyl sulfoxide, etc., N-methylpyrrolidone, and so on.

A suitable mixing ratio of the imidazole compound of formula (I) and other specific compound usually ranges from 1:300 to 300:1, preferably from 1:100 to 100:1, and more preferably from 1:50 to 5:1, by weight.

The concentration of the biocidal composition of the present invention is hard to specify as it varies depending on the crop to which the composition is applied, the method of application, the preparation form, the dose to be applied, and the like. Generally speaking, the concentrations of the imidazole compound of formula (I) and the specific compound to be combined are from 1 to 1,000 ppm and from 1 to 5,000 ppm, respectively, in the case of foliar treatment, and those in the case of soil treatment are from 10 to 10,000 g/ha and from 10 to 50,000 g/ha, respectively.

Examples of testing of the biocidal compositions according to the present invention as agricultural and horticultural fungicides are hereinafter given for illustrative purposes only but not for limitation.

TEST EXAMPLE 1

Test on preventive effect against tomato late blight

Tomato (cultivars: Ponderosa) was cultivated in a polyethylene pot having a diameter of 7.5 cm. When tomato reached the four-leaf stage, 10 ml of a solution obtained from each of test compounds adjusted to a predetermined concentration was sprayed over tomato using a spray gun. After keeping the pots in a constant temperature chamber of 22° to 24° C. over one day and one night, a zoosporangium suspension of fungi of late blight (*Phytophthora infestans*) was inoculated by spraying. Five days after the inoculation, an area of lesion on the leaves was investigated, and an index of control was determined according to the following standard. The results obtained are shown in Tables 2-1 through 2-6.

The controlling effect was determined by visually observing a degree of disease of a test plant and expressed by the following 5 grades of the index of control.

| [Index of Control] | [Degree of Disease] |
|---|---|
| 5 | No lesion is noted at all. |
| 4 | Area of lesions is less than 10% as compared to the non-treated plot. |
| 3 | Area of lesions is less than 40% as compared to the non-treated plot. |
| 2 | Area of lesions is less than 70% as compared to the non-treated plot. |
| 1 | Area of lesions is 70% or more as compared to the non-treated plot. |

TABLE 2-1

| Compound No. | Concentration (ppm) | Index of Control |
|---|---|---|
| A-6b | 0.5 | 3 |
| | 0.125 | 1 |
| B-3 | 31 | 2 |
| | 8 | 2 |
| A-6b + B-3 | 0.5 + 31 | 4 |
| | 0.5 + 8 | 4 |
| | 0.125 + 31 | 3 |
| | 0.125 + 8 | 4 |
| C-1 | 31 | 1 |
| | 8 | 1 |
| A-6b + C-1 | 0.5 + 31 | 5 |
| | 0.5 + 8 | 5 |
| | 0.125 + 31 | 2 |
| | 0.125 + 8 | 2 |

TABLE 2-2

| Compound No. | Concentration (ppm) | Index of Control |
|---|---|---|
| A-6b | 0.5 | 5 |
| | 0.125 | 3 |
| D-3 | 31 | 3 |
| | 8 | 1 |
| A-6b + D-3 | 0.5 + 31 | 5 |
| | 0.5 + 8 | 4 |
| | 0.125 + 31 | 5 |
| | 0.125 + 8 | 3 |
| E-2 | 31 | 2 |
| | 8 | 1 |
| A-6b + E-2 | 0.5 + 31 | 5 |
| | 0.5 + 8 | 5 |
| | 0.125 + 31 | 5 |
| | 0.125 + 8 | 3 |

TABLE 2-3

| Compound No. | Concentration (ppm) | Index of Control |
|---|---|---|
| A-1b | 8 | 5 |
| | 2 | 1 |
| | 0.5 | 1 |
| F-1 | 31 | 2 |
| | 8 | 1 |
| A-1b + F-1 | 8 + 31 | 5 |
| | 8 + 8 | 5 |
| | 2 + 31 | 5 |
| | 2 + 8 | 3 |
| | 0.5 + 31 | 1 |
| | 0.5 + 8 | 1 |

TABLE 2-4

| Compound No. | Concentration (ppm) | Index of Control |
|---|---|---|
| A-1b | 8 | 5 |
| | 2 | 3 |
| | 0.5 | 2 |
| G-1 | 8 | 3 |
| | 2 | 1 |
| A-1b + G-1 | 8 + 8 | 5 |
| | 8 + 2 | 5 |
| | 2 + 8 | 5 |
| | 2 + 2 | 4 |
| | 0.5 + 8 | 5 |
| | 0.5 + 2 | 3 |

TABLE 2-5

| Compound No. | Concentration (ppm) | Index of Control |
|---|---|---|
| A-1b | 0.5 | 4 |
| | 0.125 | 1 |
| D-3 | 31 | 1 |
| | 8 | 1 |
| A-1b + D-3 | 0.5 + 31 | 5 |
| | 0.5 + 8 | 5 |
| | 0.125 + 31 | 4 |
| | 0.125 + 8 | 4 |

TABLE 2-6

| Compound No. | Concentration (ppm) | Index of Control |
|---|---|---|
| A-1b | 0.5 | 4 |
| | 0.125 | 3 |
| H-1 | 8 | 3 |
| | 2 | 3 |
| A-1b + H-1 | 0.5 + 8 | 5 |
| | 0.5 + 2 | 5 |
| | 0.125 + 8 | 3 |
| | 0.125 + 2 | 4 |

TEST EXAMPLE 2

Test on preventive effect against tomato late blight

A test similar to Test Example 1 was carried out. The degree of disease has visually observed to determine the index of control according to the following standard for evaluation. The results obtained are shown in Tables 3-1 through 3-3.

| Standard for Evaluation: | |
|---|---|
| [Index of Control] | [Degree of Disease] |
| 7 | No lesion is observed at all. |
| 6 | Area or length of lesions is less than 5% of that of the non-treated plot. |
| 5 | Area or length of lesions is from 5 to less than 10% of that of the non-treated plot. |
| 4 | Area or length of lesions is from 10 to less than 25% of that of the non-treated plot. |
| 3 | Area or length of lesions is from 25 to less than 40% of that of the non-treated plot. |
| 2 | Area or length of lesions is from 40 to less than 70% of that of the non-treated plot. |
| 1 | Area or length of lesions is 70% or more of that of the non-treated plot. |

TABLE 3-1

| Compound No. | Concentration (ppm) | Index of Control |
|---|---|---|
| A-1b | 0.125 | 4 |
| A-12b | 0.125 | 2 |
| I-1 | 2 | 2 |
| | 0.5 | 1 |
| A-1b + I-1 | 0.125 + 2 | 5 |
| | 0.125 + 0.5 | 7 |
| A-12b + I-1 | 0.125 + 2 | 7 |
| | 0.125 + 0.5 | 6 |

TABLE 3-2

| Compound No. | Concentration (ppm) | Index of Control |
|---|---|---|
| A-1b | 0.5 | 4 |
| I-2 | 31 | 5 |
| H-1 | 31 | 4 |
| Q-1 | 8 | 1 |
| A-1b + I-2 | 0.5 + 31 | 7 |
| A-1b + H-1 | 0.5 + 31 | 7 |
| A-1b + Q-1 | 0.5 + 8 | 7 |

TABLE 3-3

| Compound No. | Concentration (ppm) | Index of Control |
|---|---|---|
| A-12b | 0.5 | 4 |
| K-1 | 500 | 2 |
| I-2 | 8 | 3 |
| | 2 | 1 |
| A-12b + K-1 | 0.5 + 500 | 7 |
| A-12b + I-2 | 0.5 + 8 | 7 |
| | 0.5 + 2 | 7 |

TEST EXAMPLE 3

Test of curative effect on tomato late blight

Tomato (cultivars: Ponderosa) was cultivated in a polyethylene pot having a diameter of 7.5 cm. When tomato reached the four-leaf stage, a zoosporangium suspension of fungi of late blight (*Phytophthora infestans*) was inoculated by spraying. Six hours later, 10 ml of a solution of each of test compounds at a predetermined concentration has sprayed onto the tomato plant using a spray gun. After keeping the pots in a constant temperature chamber of 22° to 24° C. for 5 days, an area of lesions was examined to obtain the index of control according to the standard of Test Example 2. The results obtained are shown in Tables 4-1 through 4-3.

TABLE 4-1

| Compound No. | Concentration (ppm) | Index of Control |
|---|---|---|
| A-1b | 500 | 4 |
| | 125 | 4 |
| I-1 | 8 | 3 |
| | 2 | 1 |
| A-1b + I-1 | 500 + 8 | 7 |
| | 500 + 2 | 7 |
| | 125 + 8 | 7 |
| | 125 + 2 | 5 |

TABLE 4-2

| Compound No. | Concentration (ppm) | Index of Control |
|---|---|---|
| A-1b | 500 | 3 |
| | 125 | 1 |
| I-2 | 31 | 4 |
| H-1 | 8 | 3 |

TABLE 4-2-continued

| Compound No. | Concentration (ppm) | Index of Control |
|---|---|---|
| Q-1 | 8 | 4 |
| A-1b + I-2 | 500 + 31 | 6 |
| | 125 + 31 | 6 |
| A-1b + H-1 | 500 + 8 | 5 |
| | 125 + 8 | 6 |
| A-1b + Q-1 | 500 + 8 | 6 |

TABLE 4-3

| Compound No. | Concentration (ppm) | Index of Control |
|---|---|---|
| A-12b | 8 | 2 |
| | 2 | 1 |
| I-2 | 31 | 2 |
| H-1 | 31 | 5 |
| | 8 | 1 |
| Q-1 | 31 | 2 |
| A-12b + I-2 | 8 + 31 | 6 |
| | 2 + 31 | 5 |
| A-12b + H-1 | 8 + 31 | 7 |
| | 8 + 8 | 4 |
| A-12b + Q-1 | 8 + 31 | 6 |
| | 2 + 31 | 6 |

TEST EXAMPLE 4

Test of curative effect on cucumber downy mildew

Cucumber (cultivars: Suyo) was cultivated in a polyethylene pot having a diameter of 7.5 cm. When cucumber reached the two-leaf stage, a spore suspension of fungi of downy mildew (*Pseudoperonospora cubensis*) was inoculated by spraying. Twenty-four hours after the inoculation, 10 ml of a solution of each of test compounds adjusted to a predetermined concentration was sprayed over cucumber using a spray gun. After keeping the pots in a constant temperature chamber of 22° to 24° C. for 6 days, an area of lesion on the first leaf was visually observed to determine the index of control according to the standard of Test Example 2. The results obtained are shown in Tables 5-1 through 5-3.

TABLE 5-1

| Compound No. | Concentration (ppm) | Index of Control |
|---|---|---|
| A-1b | 0.5 | 3 |
| | 0.125 | 1 |
| A-12b | 0.5 | 3 |
| | 0.125 | 1 |
| I-1 | 8 | 3 |
| | 2 | 1 |
| A-1b + I-1 | 0.5 + 8 | 6 |
| | 0.5 + 2 | 4 |
| | 0.125 + 8 | 4 |
| | 0.125 + 2 | 1 |
| A-12b + I-1 | 0.5 + 8 | 5 |
| | 0.5 + 2 | 4 |
| | 0.125 + 8 | 4 |
| | 0.125 + 2 | 1 |

TABLE 5-2

| Compound No. | Concentration (ppm) | Index of Control |
|---|---|---|
| A-1b | 0.5 | 1 |
| | 0.125 | 1 |
| M-1 | 125 | 1 |
| Q-1 | 31 | 5 |
| | 8 | 2 |
| A-1b + M-1 | 0.5 + 125 | 5 |
| | 0.125 + 125 | 3 |
| A-1b + Q-1 | 0.5 + 31 | 7 |

TABLE 5-2-continued

| Compound No. | Concentration (ppm) | Index of Control |
|---|---|---|
| | 0.5 + 8 | 4 |

TABLE 5-3

| Compound No. | Concentration (ppm) | Index of Control |
|---|---|---|
| A-12b | 0.5 | 3 |
| M-1 | 500 | 1 |
| | 125 | 1 |
| I-2 | 8 | 2 |
| | 2 | 1 |
| H-1 | 8 | 3 |
| | 2 | 1 |
| Q-1 | 31 | 3 |
| | 8 | 2 |
| A-12b + M-1 | 0.5 + 500 | 6 |
| | 0.5 + 125 | 6 |
| A-12b + I-2 | 0.5 + 8 | 5 |
| | 0.5 + 2 | 5 |
| A-12b + H-1 | 0.5 + 8 | 6 |
| | 0.5 + 2 | 6 |
| A-12b + Q-1 | 0.5 + 31 | 6 |
| | 0.5 + 8 | 6 |

TEST EXAMPLE 5

Test on preventive effect against cucumber gray mold

Cucumber (cultivars: Suyo) was cultivated in a polyethylene pot having a diameter of 7.5 cm. When cucumber reached the two-leaf stage, 10 ml of a solution obtained from each of test compounds adjusted to a predetermined concentration has sprayed over cucumber using a spray gun. After keeping the pots in a constant temperature chamber of 22° to 24° C. over one day and one night, a mycelial disc having a diameter of 5 mm of fungi of gray mold (*Botrytis cinerea*) was inoculated on the first leaf. Three days after the inoculation, a length of lesion was investigated, and an index of control was determined according to the standard of Test Example 2. The results shown in Table 6 were obtained.

TABLE 6

| Compound No. | Concentration (ppm) | Index of Control |
|---|---|---|
| A-1b | 500 | 1 |
| | 125 | 1 |
| J-1 | 8 | 2 |
| | 2 | 1 |
| O-1 | 31 | 3 |
| A-1b + J-1 | 500 + 8 | 6 |
| | 500 + 2 | 4 |
| A-1b + O-1 | 500 + 31 | 5 |
| | 125 + 31 | 5 |

TEST EXAMPLE 6

Test on preventive effect against rice sheath blight

Rice plant (cultivars: Chukyo Asahi) was cultivated in a polyethylene pot having a diameter of 7.5 cm. When rice plant reached the five-leaf stage, 20 ml of a solution obtained from each of test compounds adjusted to a predetermined concentration was sprayed over rice plant using a spray gun. After keeping the pots in a constant temperature chamber of 22° to 24° C. over one day and one night, rice straw in which fungi of sheath blight (*Rhizoctonia solani*) had been previously incubated was set between leaf sheath portions to inoculate. After keeping the pots in an inoculation room having a temperature of 28° C. and humidity of 100% for 5 days, a length of lesion was investigated, and an index of control was determined according to the standard of Test Example 2. The results shown in Table 7 were obtained.

TABLE 7

| Compound No. | Concentration (ppm) | Index of Control |
|---|---|---|
| A-1b | 500 | 1 |
| | 125 | 1 |
| A-12b | 500 | 1 |
| | 125 | 1 |
| P-1 | 31 | 4 |
| A-1b + P-1 | 500 + 31 | 7 |
| | 125 + 31 | 7 |
| A-12b + P-1 | 500 + 31 | 7 |
| | 125 + 31 | 7 |

TEST EXAMPLE 7

Antimicrobial test (phytopathogenic fungi)

Mycelial disc (agar punching) of preincubated *Pythium aphanidermatum* was transplanted on potato-dextrose agar medium (PDA medium) containing 100 ppm of streptomycin and a predetermined concentration of each of test compounds. After incubation at 22° C. for 48 hours, a diameter of mycellium was measured. Inhibition of hyphal growth (%) was determined by the following equation. The results shown in Table 8 were obtained.

inhibition of hyphal growth (%) =

$$100 - \frac{\text{Diameter of mycelium in treated plot}}{\text{Diameter of mycelium in non-treated plot}} \times 100$$

TABLE 8

| Compound No. | Concentration (ppm) | Inhibition of Hyphal Growth (%) |
|---|---|---|
| A-1b | 1 | 91 |
| | 0.1 | 85 |
| A-12b | 1 | 85 |
| | 0.1 | 88 |
| L-1 | 100 | 54 |
| A-1b + L-1 | 1 + 100 | 100 |
| | 0.1 + 100 | 100 |
| A-12b + L-1 | 1 + 100 | 100 |
| | 0.1 + 100 | 100 |

Formulation Examples of the biocidal composition according to the present invention are described below, but the present invention is not deemed to be limited thereto.

FORMULATION EXAMPLE 1

| | |
|---|---|
| Compound No. A-1b | 5 parts by weight |
| Compound No. D-3 | 45 parts by weight |
| Kaolin | 40 parts by weight |
| Calcium lignin sulfonate | 7 parts by weight |
| Dialkylsulfosuccinate | 3 parts by weight |

The above components are uniformly mixed to prepare a wettable powder.

FORMULATION EXAMPLE 2

A wettable powder can be prepared in the same manner as in Formulation Example 1, except for replacing Compound No. A-1b with 25 parts by weight of Compound No. A-12b and replacing Compound No. D-3 with 25 parts by weight of Compound No. I-1.

FORMULATION EXAMPLE 3

A wettable powder can be prepared in the same manner as in Formulation Example 1, except for replacing Compound No. D-3 with Compound No. K-1.

FORMULATION EXAMPLE 4

| | |
|---|---|
| Compound No. A-1b | 5 parts by weight |
| Compound No. G-1 | 15 parts by weight |
| Calcium carbonate | 20 parts by weight |
| Kaolin | 52 parts by weight |
| Calcium lignin sulfonate | 4 parts by weight |
| Polyoxyethylene alkylaryl ether | 4 parts by weight |

The above components are uniformly mixed to prepare a wettable powder.

FORMULATION EXAMPLE 5

A wettable powder can be prepared in the same manner as in Formulation Example 4, except for replacing Compound No. G-1 with Compound No. F-1.

FORMULATION EXAMPLE 6

A wettable powder can be prepared in the same manner as in Formulation Example 4, except for replacing Compound No. G-1 with Compound No. O1.

FORMULATION EXAMPLE 7

| | |
|---|---|
| Compound No. A-6b | 5 parts by weight |
| Compound No. B-3 | 5 parts by weight |
| Diatomaceous earth | 84 parts by weight |
| Dialkylsulfosuccinate | 2 parts by weight |
| Polyoxyethylene alkylphenyl ether sulfate | 4 parts by weight |

The above components are uniformly mixed to prepare a wettable powder.

FORMULATION EXAMPLE 8

A wettable powder can be prepared in the same manner as in Formulation Example 7, except for replacing Compound No. B-3 with Compound No. M-1.

FORMULATION EXAMPLE 9

| | |
|---|---|
| Kaolin | 78 parts by weight |
| Sodium β-naphthalenesulfonate-formaldehyde condensate | 2 parts by weight |
| Polyoxyethylene alkylaryl sulfate | 5 parts by weight |
| Hydrated amorphous silicon dioxide | 15 parts by weight |

A mixture consisting of the above components is mixed with Compound No. A-1b and Compound No. I-1 at a weight mixing ratio of 8:1:1 to prepare a wettable powder.

FORMULATION EXAMPLE 10

A wettable powder can be prepared in the same manner as in Formulation Example 9, except for replacing Compound No. I-1 with Compound No. I-7.

FORMULATION EXAMPLE 11

| | |
|---|---|
| Compound No. A-12b | 0.25 parts by weight |
| Compound No. I-1 | 0.25 parts by weight |
| Calcium carbonate | 99.0 parts by weight |
| Lower alcohol phosphate | 0.5 parts by weight |

The above components are uniformly mixed to prepare a dust.

FORMULATION EXAMPLE 12

| | |
|---|---|
| Compound No. A-6b | 2.5 parts by weight |
| Compound No. H-1 | 2.5 parts by weight |
| Xylene | 75 parts by weight |
| Polyoxyethylene alkylaryl ether | 20 parts by weight |

The above components are mixed and dissolved to prepare an emulsifiable concentrate.

FORMULATION EXAMPLE 13

| | |
|---|---|
| Compound No. A-1b | 0.5 parts by weight |
| Compound No. I-1 | 0.5 parts by weight |
| Bentonite | 20 parts by weight |
| Kaolin | 74 parts by weight |
| Sodium lignin sulfonate | 5 parts by weight |

To the above components is added an adequate amount of water for granulation, and the mixture is mixed and granulated to prepare granules.

FORMULATION EXAMPLE 14

| | |
|---|---|
| Compound No. A-1b | 2.5 parts by weight |
| Compound No. D-3 | 22.5 parts by weight |
| Kerosene | 63 parts by weight |
| A mixture of polyoxyethylene phenylphenol derivative and polyoxyethylene sorbitan alkylate | 12 parts by weight |

The above components are mixed and finely pulverized to prepare a suspension concentrate.

FORMULATION EXAMPLE 15

A suspension concentrate can be prepared in the same manner as in Formulation Example 14, except for replacing Compound No. D-3 with Compound No. E-2.

While the invention has been described in detail and with reference to specific embodiments thereof, it will be apparent to one skilled in the art that various changes and modifications can be made therein without departing from the spirit and scope thereof.

What is claimed is:

1. A biocidal composition containing, as active ingredients, at least one imidazole compound represented by formula (I):

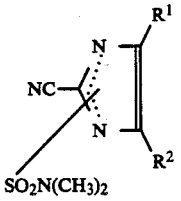

(I)

wherein $R^1$ represents a phenyl group, a halogen-substituted phenyl group, an alkyl group, or a halogen-substituted alkyl group; and $R^2$ represents a halogen atom, and at least one compound selected from the group consisting of azole compounds, quinoxaline compounds, dithiocarbamate compounds, organic chlorine compounds, benzimidazole compounds, pyridinamine compounds, cyanoacetamide compounds, phenylamide compounds, sulfenic acid compounds, copper compounds, isoxazole compounds, organophosphorus compounds, N-halogenothioalkyl compounds, dicarboximide compounds, benzanilide compounds, benzamide compounds, piperazine compounds, pyridine compounds, pyrimidine compounds, piperidine compounds, morpholine compounds, organotin compounds, urea compounds, cinnamic acid compounds, carbamate compounds, pyrethroid compounds, benzoylurea compounds, thiazolidine compounds, thiadiazine compounds, nereistoxin derivatives, pyridazinone compounds, and spores of *Bacillus thuringiensis* and crystalline toxin produced thereby.

2. A biocidal composition as claimed in claim 1, wherein the imidazole compound is represented by formula (I'):

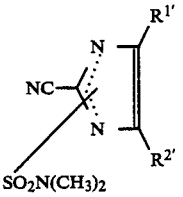

(I')

wherein $R^{1'}$ represents a phenyl group or a halogen-substituted alkyl group; and $R^{2'}$ represents a chlorine atom.

3. A biocidal composition as claimed in claim 1, wherein the compound which is used in admixture with the imidazole compounds represented by formula (I) is at least one compound selected from the group consisting of azole compounds, quinoxaline compounds, dithiocarbamate compounds, organic chlorine compounds, benzimidazole compounds, pyridinamine compounds, cyanoacetamide compounds, phenylamide compounds, sulfenic acid compounds, copper compounds, isoxazole compounds, organophosphorus compounds, dicarboximide compounds, benzanilide compounds, and benzamide compounds.

* * * * *